United States Patent [19]

Giannessi et al.

[11] Patent Number: 5,412,113

[45] Date of Patent: May 2, 1995

[54] PROCESS FOR MANUFACTURING L-(−)-CARNITINE FROM A WASTE PRODUCT HAVING OPPOSITE CONFIGURATION

[75] Inventors: Fabio Giannessi, Rome; Maria L. Bolognesi, Bologna; Maria O. Tinti; Francesco De Angelis, both of Rome, all of Italy

[73] Assignee: Sigma-Tau Industrie Farmaceutiche Riunite S.p.A., Rome, Italy

[21] Appl. No.: 170,764

[22] Filed: Dec. 21, 1993

[30] Foreign Application Priority Data

Dec. 21, 1992 [IT] Italy .............................. RM92A0915

[51] Int. Cl.⁶ .......................................... C07D 305/12
[52] U.S. Cl. ..................................................... 549/328
[58] Field of Search ......................................... 549/328

[56] References Cited

U.S. PATENT DOCUMENTS 5,200,526 4/1993 Arnold et al. ..................... 549/328

Primary Examiner—C. Warren Ivy
Assistant Examiner—Ba K. Trinh
Attorney, Agent, or Firm—Oblon, Spivak, McClelland, Maier & Neustadt

[57] ABSTRACT

The present invention relates to a proces for manufacturing L-(−)-carnitine from D-(+)-carnitine or a derivative thereof. D-(+)-carnitine is esterified in order to protect the carboxyl group and subsequently converted to an acyl derivative. The acyl derivative is then converted to a lactone of L-(−)-carnitine. Finally, the lactone is reopened to obtain L-(−)-carnitine.

7 Claims, No Drawings

PROCESS FOR MANUFACTURING L-(−)-CARNITINE FROM A WASTE PRODUCT HAVING OPPOSITE CONFIGURATION

BACKGROUND OF THE INVENTION

1. Field of the Invention

The present invention relates to a process for manufacturing L-(−)-carnitine from a starting compound containing an asymmetrical carbon atom having a configuration opposite to that of L-(−)-carnitine. The process of the present invention overcomes the drawbacks of conventional processes which first convert a starting compound into an achiral intermediate, generally crotonobetaine or gamma-butyrobetaine, and then convert the achiral intermediate to L-(−)-carnitine. The process of the present invention uses D-(+)-carnitine or a derivative thereof as a starting compound.

2. Discussion of the Background

Carnitine contains a single center of asymmetry and therefore exists as two enantiomers, designated D-(+)-carnitine and L-(−)-carnitine. Of these, only L-(−)-carnitine is found in living organisms, where it functions as a vehicle for transporting fatty acids across mitochondrial membranes. Whilst L-(−)-carnitine is the physiologically-active enantiomer, racemic D,L-carnitine has conventionally been used as a therapeutic agent. It is now recognized, however, that D-(+)-carnitine is a competitive inhibitor of carnitine acyltransferases, and that it diminishes the level of L-(−)-carnitine in myocardium and skeletal muscle.

It is therefore essential that only L-(−)-carnitine be administered to patients undergoing haemodialysis treatment or treatment for cardiac or lipid metabolism disorders. The same requirement applies to the therapeutic utilization of acyl derivatives of carnitine for treating disorders of the cerebral metabolism, peripheral neuropathies, peripheral vascular diseases and the like. These disorders are typically treated with acetyl L-(−)-carnitine and propionyl L-(−)-carnitine, which are obtained by acylating L-(−)-carnitine.

Various chemical procedures have been proposed for the industrial-scale production of carnitine. Unfortunately, these procedures are not stereospecific and produce racemic mixtures of D-(+)- and L-(−)-isomers. It is thus necessary to apply resolution methods in order to separate the enantiomeric constituents of the racemate.

Typically, the D,L-racemic mixture is reacted with an optically active acid (e.g. D-(−)-tartaric acid, D-(+)-camphorsulfonic acid, (+)-dibenzoyl-D-(−)-tartaric acid, N-acetyl-L-(+)-glutamic acid and D-(+)-camphoric acid) to obtain two diastereoisomers which can be separated from each other. In the classic process disclosed in U.S. Pat. No. 4,254,053, D-(+)-camphoric acid is used as the resolution agent of a racemic mixture of D,L-carnitinamide, obtaining D-(+)-carnitinamide as a by-product, and L-(−)-carnitinamide which, by hydrolysis, gives L-(−)-carnitine.

However, these resolution procedures are complex and costly, and in all cases result in the production of equimolar quantities of L-(−)-carnitine and D-(+)-carnitine or a precursor thereof as by-product, having configuration opposite to that of L-(−)-carnitine. Several microbiological processes have recently been proposed for producing L-(−)-carnitine via stereospecific transformation of achiral derivatives obtained from the huge amounts of D-(+)-carnitine (or of a precursor thereof, such as D-(+)-carnitinamide) which are generated as by-products in the industrial production of L-(−)-carnitine.

These processes are generally predicated upon the stereospecific hydration of crotonobetaine to L-(−)-carnitine, and differ principally by virtue of the particular microorganism employed to accomplish the biotransformation of interest. See, for example, the processes disclosed in: EP 0 121 444 (HAMARI), EP 0 122 794 (AJINOMOTO), EP 0 148 132 (SIGMA-TAU), JP 275689/87 (BIORU), JP 61067494 (SEITETSU), JP 61234794 (SEITETSU), JP 61234788 (SEITETSU), JP 61271996 (SEITETSU), JP 61271995 (SEITETSU), EP 0 410 430 (LONZA), EP 0 195 944 (LONZA), EP 0 158 194 (LONZA), and EP 0 457 735 (SIGMA-TAU).

On the other hand, JP 62044189 (SEITETSU) discloses a process for stereoselectively producing L-(−)-carnitine starting from gamma-butyrobetaine, which is in turn obtained enzymically from crotonobetaine.

All of these processes have several drawbacks. First, D-(+)-carnitine must first be converted to an achiral compound (crotonobetaine, gamma-butyrobetaine) before it can be used as the starting compound in all of the aforesaid microbiological processes.

In addition, the microbiological procedures proposed to date have not proven practicable for manufacturing L-(−)-carnitine on an industrial scale for one or more of the following reasons:

(i) the yield of L-(−)-carnitine is extremely low;
(ii) the microorganisms must be cultivated in a costly nutritive medium;
(iii) the microorganism can only tolerate low concentrations [up to 2–3% (w/v)] of crotonobetaine;
(iv) side reactions occur, such as the reduction of crotonobetaine to gamma-butyrobetaine or the oxidation of L-(−)-carnitine to 3-dehydrocarnitine. These side reactions reduce the final yield of L-(−)-carnitine.

SUMMARY OF THE INVENTION

Accordingly, one object of the present invention is to provide an efficient method for producing L-(−)-carnitine from a derivative of D-(−)-carnitine.

The process of the present invention overcomes all of the aforesaid drawbacks of the known processes, allowing high yields of L-(−)-carnitine to be obtained starting from a by-product having configuration opposite to that of L-(−)-carnitine with no need to first convert the starting by-product into an achiral intermediate.

DETAILED DESCRIPTION OF THE PREFERRED EMBODIMENTS

The process of the invention is illustrated in the following reaction scheme:

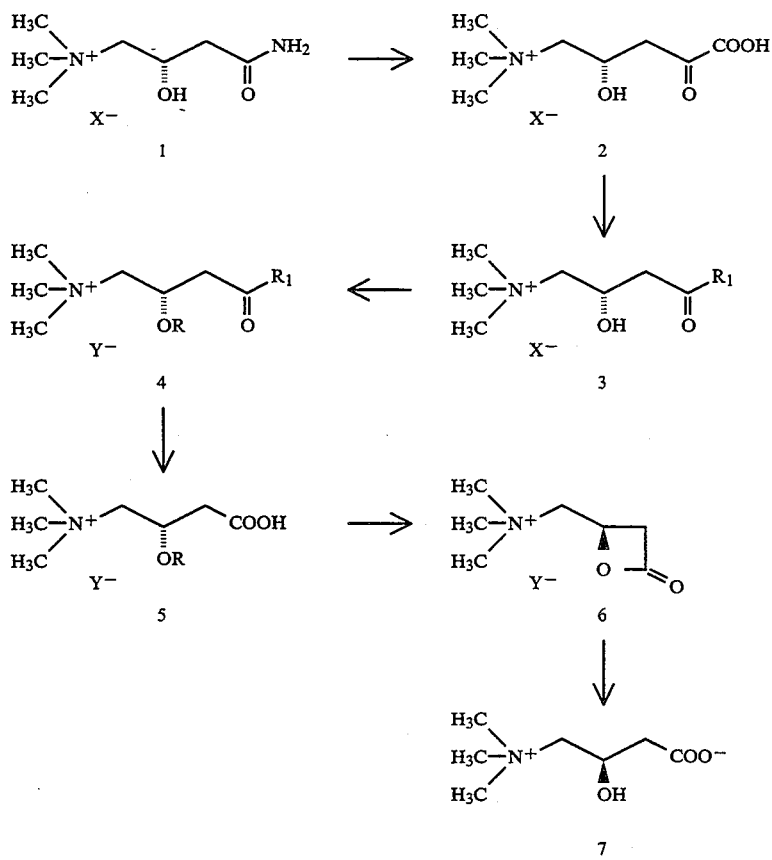

With reference to the reaction scheme, the D-(+)-carnitinamide salt 1, wherein X is any suitable counterion is hydrolyzed to D-(+)-carnitine 2 via conventional procedures (see, for example JP 287065/1989, incorporated herein by reference). X is suitably a halogen, preferably chloride; phosphate; perchlorate; metaperiodate; tetraphenylborate; an alkylsulfonate having 1-12 carbon atoms, preferably dodecylsulphonate; trifluoroacetate; tetrahalogenborate; fumarate or an alkylsulphate having 10-14 carbon atoms.

D-(+)-carnitine 2 is then converted to the ester 3 in order to protect the carboxyl group. Suitable esters 3 are those wherein $R_1$ is (1) a straight or branched alkoxy group having 1-11 carbon atoms or (2) an arylalkoxy or diarylalkoxy group wherein the aryl is a monocyclic or bicyclic aryl and the alkyl has 1-4 carbon atoms. Suitable monocyclic or bicyclic aryl groups contain 5-12 carbon atoms and can be optionally substituted with a lower alkyl group having 1-4 carbon atoms; an alkoxy group having 1-4 carbon atoms; halogen, preferably fluorine or chlorine; a nitro group or an amino group. Suitable arylalkoxy or diarylalkoxy groups include p-methoxybenzyloxy, 1-naphthalenemethoxy, 2-naphthalenemethoxy, and diphenylmethoxy. A particularly preferred arylalkoxy group is benzyloxy.

The esterification of 2 to 3 is carried out via conventional procedures. For instance, when $R_1$ is benzyloxy, the preparation of D-(+)-carnitine benzyl ester is carried out as disclosed in Blochim. Biophys. Acta (1967) 137:98, incorporated herein by reference.

The ester 3 is then converted to the acyl derivative 4. Y, which can be the same as X, is preferably a counterion imparting solubility to 4. OR is a leaving group wherein R is an alkylsulfonyl group having 1-12 carbon atoms, formyl or trifluoroacetyl. Preferably, the alkylsulfonyl group is selected from methanesulfonyl (mesyl), p-toluenesulfonyl (tosyl), p-bromobenzenesulfonyl (brosyl), p-nitrobenzenesulfonyl (nosyl), trifluoromethanesulfonyl (triflyl), nonafluoromethanesulfonyl (nonaflyl) and 2,2,2-trifluoroethanesulfonyl (tresyl). Mesyl is particularly preferred.

The acylation of 3 to 4 is carried out by reacting the ester 3 with an acylating agent RY wherein Y is halogen, or RY itself is an anhydride and R is an acyl group as defined above. Preferably RY is the chloride of the selected acyl group.

The acylation reaction is suitably carried out in pyridine, alkylpyridines, or other basic solvents such as triethylamine or in a mixture of an anhydrous, inert organic solvent such as acetonitrile or methylene chloride with a base such as pyridine, lutidine, picoline or polyvinylpyridine.

The acylating agent is suitably added at ratios ranging from 1:1 to 1:10, preferably 1:3. The resulting reaction mixture is kept under stirring at temperatures comprised between 0° C. and 50° C., for 1-24 hours. Compound 4 is isolated by precipitation with a suitable solvent such as ethyl ether or hexane and purified by dissolving it in water and extracting with an organic solvent.

The carboxyl group is restored into compound 4 via known procedures, to yield acyl D-(+)-carnitine 5. In some instances, if needed, compound 4 is subjected to hydrogenation.

Hydrogenation of 4 is suitably carried out in an aqueous solution, at pH 2-4, or in methanol at 0° C.-25° C., for 1-8 hours, at 1-4 hydrogen atmospheres, in the presence of a hydrogenation catalyst such as 5% or 10% Pd/C. Acyl D-(+)-carnitine 5 can be isolated by filtering off the catalyst and lyophilizing or concentrating the aqueous solution.

Acyl D-(+)-carnitine 5 is then converted to the lactone 6 of L-(−)-carnitine. The lactonization is suitably carried out in an aqueous basic environment: either with NaHCO$_3$ (ratio 1:1) or with an AMBERLITE IRA-402 (manufactured by Rohm & Haas Co., GERMANY) basic resin activated in HCO$_3^-$ form or with an LA2 resin (Rohm & Haas). The lactone is isolated by evaporating the aqueous solution or precipitating it as a salt (for example, as tetraphenylborate or reineckate).

Finally, lactone 6 is suitably converted to L-(−)-carnitine inner salt 7. The lactone is dissolved in water and the resulting solution treated with a base such as NaHCO$_3$ (ratio 1:1), for 8–24 hours.

L-(−)-carnitine can suitably be purified from the salts which are formed from the X$^-$ anion, from the excess, if any, of the acyl halogenide, from pyridine, and the like, by chromatographing the aqueous solution on a strongly acidic resin such as IR 120 (Rohm & Haas), eluting with water and then with NH$_4$OH, or alternatively eluting first on a strongly basic resin such as AMBERLITE IRA 402 (Rohm & Haas) activated in OH form and thereafter on a weakly acid resin such as AMBERLITE IRC-50 (Rohm & Haas).

It should be understood that, whereas the process disclosed above has been described, for the sake of clarity, as a sequence of six distinct operating steps, the corresponding industrial process consists of four steps only. When the process of the present invention is carried out as an industrial process, the acyl D-(+)-carnitine ester 4 can be directly converted to L-(−)-carnitine inner salt 7 without isolating either the acyl D-(+)-carnitine 5 or the lactone 6.

In fact, the ester of acyl D-(+)-carnitine 4 is hydrogenated and the hydrogenation catalyst filtered off. The resulting aqueous solution is brought to pH 7–9, preferably 8–9 and kept at this pH value for 30–50 hours yielding L-(−)-carnitine. L-(−)-carnitine thus obtained is purified by removing the salts by treatment with acidic and basic resins.

In the following example which describes one embodiment of the process of the invention, the intermediate compounds 4, 5 and 6 were isolated so as to exhaustively characterize them from a physico-chemical standpoint, insofar as these intermediates are novel compounds.

It will be, however, apparent to any expert in organic synthesis that the industrial process comprises the following steps only:

(a) hydrolysis of D-(+)-carnitinamide 1 to D-(+)-carnitine 2;
(b) esterification of D-(+)-carnitine 2 to the ester 3 to protect the carboxyl group;
(c) acylation of the hydroxyl group of ester 3 with an acylating agent RY wherein Y is a halogen or RY itself an anhydride, with the resulting formation of a leaving group OR wherein R has the previously defined meanings, thus obtaining the ester 4 of D-(+)-carnitine; and
(d) conversion of 4 to L-(−)-carnitine inner salt 7.

Having generally described this invention, a further understanding can be obtained by reference to certain specific examples which are provided herein for purposes of illustration only and are not intended to be limiting unless otherwise specified.

In the following example, the conversion of D-(+)-carnitinamide to D-(+)-carnitine and the conversion of the latter compound to ester 3 are not described for the sake of brevity and since those conversions can be carried out via procedures well-known to any expert in organic synthesis.

Moreover, with reference to the numbering of the compound show in the reaction scheme, the lower-case letters "a", "b" and "c" are used in the example to indicate X$^-$ = perchlorate, chloride and methanesulfonate, respectively.

EXAMPLE

Preparation of methanesulfonyl D-(+)-carnitine benzyl ester perchlorate (4a).

Methanesulfonyl chloride (25.77g; 225 mmoles) was added in the space of five minutes to a solution of D-(+)-carnitine benzylester perchlorate (24.4g; 75 mmoles) in anhydrous pyridine (100 mL) cooled in an ice bath. At the end of the addition, the solution was kept under stirring at room temperature for 1 hour and 45 minutes. The solution was then poured into an Erlenmeyer flask containing 500 mL Et$_2$O under stirring.

The oily precipitate obtained by decantation of Et$_2$O was taken up with CH$_2$Cl$_2$ (300 mL), the solution was washed with 2N HCl (4×5 mL), saturated solution of NaCl (1×20 mL) and dried over anhydrous Na$_2$SO$_4$.

Following evaporation of the organic phase, 22 g of an amorphous solid were obtained. Yield 70%. Differential thermal analysis: it decomposes at about 180° C. $[\alpha]^{25}_D = +20.0°$ [c=1% MeOH)

| TLC = silica gel | Eluant = CHCl$_3$/MeOH/iPrOH/H$_2$O/AcOH 42/28/7/10.5/10.5 Rf = 0.5 | | | |
|---|---|---|---|---|
| Elementary analysis for C$_{15}$H$_{24}$ClNO$_9$S | | | | |
| | C % | H % | N % | Cl % |
| Calculated | 41.91 | 5.63 | 3.25 | 8.25 |
| Found | 41.81 | 4.72 | 3.28 | 8.10 |

$^1$H NMR ((CD$_3$)$_2$CO): δ7.45–7.30 (m, 5H, aromatics); 5.71–5.62 (m, 1H, —CHOMs); 5.20 (s, 2H, —CH$_2$Ph); 4.24–4.02 (m, 2H, —CH$_2$N$^+$Me$_3$); 3.47 (s, 9H, —N$^+$-Me$_3$); 3.30 (s, 3H, CH$_3$SO$_3$—) 3.20 (2H, d, —CH$_2$COO$^-$)
$^{13}$C NMR ((CD$_3$)$_2$ CO): δ169.413; 136.685; 129.153; 71.902 67.496; 54.683; 39.387; 38.640
IR (KBr)=υ(cm$^{-1}$) 1735 (—C=O), 1341 and 1174 (CH$_3$SO$_3$—)
HPLC
Column=Nucleosil 5-SA; diameter=4 mm; length=200 mm
Eluant=CH$_3$CN/KH$_2$PO$_4$ 50 mM (65/35) pH=3.5 with H$_3$PO$_4$
Flow rate=0.75 ml/min
Retention time=9.35 min
Detector=RI Waters 410

Preparation of methanesulfonyl D-(+)-carnitine benzyl ester chloride (4b).

18.3 g (42.6 mmoles) of methanesulfonyl D-(+)-carnitine benzyl ester perchlorate were dissolved in 300 mL CH$_3$OH and few mL CH$_3$CN (till complete dissolution). The solution thus obtained was percolated through AMBERLYST A-21 resin (300 g) activated by percolating therethrough 1N HCl, then H$_2$O till neutrality and finally CH$_3$OH. Following methanol evaporation, 15.5 of a solid product were obtained. Yield:

quantitative. Differential thermal analysis: it decomposes at about 150° C. $[\alpha]^{25}_D = +22.6°$ [c=1% MeOH]

TLC = silica gel  Eluant = CHCl$_3$/MeOH/iPrOH/H$_2$O/AcOH
42/28/7/10.5/10.5
Rf = 0.5

Elementary analysis for C$_{15}$H$_{24}$ClNO$_5$S

|  | C % | H % | N % | Cl % |
|---|---|---|---|---|
| Calculated (+3.3% di · H$_2$O) | 47.62 | 6.76 | 3.70 | 9.37 |
| Found | 47.88 | 7.52 | 3.77 | 9.04 |

$^1$H NMR (D$_2$O): δ7.50–7.45 (m, 5H, aromatics); 5.70–5.62 (m, 1H, —CHOMs); 5.40–5.30 (m, 2H, —CH$_2$Ph); 4.03–3.72 (m, 2H, —CH$_2$N$^+$Me$_3$); 3.25 (s, 3H, CH$_3$SO$_3$—) 3.22 (s, 9H —N$^+$Me$_3$); 3.15 (2H, d, —CH$_2$COO$^-$)

$^{13}$C NMR (D$_2$O): δ172.789; 137.950; 131.695; 73.929; 70.651; 56.831; 41.475; 40.920

IR (pure)=ν(cm$^{-1}$) 1734 (—C=O), 1340 and 1174 (CH$_3$SO$_3$$^-$)

HPLC
Column=Nucleosil 5-SA; diameter=4 mm; length=200 mm
Eluant=CH$_3$CN/KH$_2$PO$_4$ 50 mM (65/35) pH=3.5 with H$_3$PO$_4$
Flow rate=0.75 ml/min
Retention time=9.41 min
Detector=RI Waters 410

Preparation of methanesulfonyl D-(+)-carnitine perchlorate (5a).

10% Pd/C (300 mg) was added to a solution of methanesulfonyl D-(+)-carnitine benzyl ester perchlorate (3.0 g; 7 mmoles) in CH$_3$OH (50 mL).

The resulting mixture was kept under stirring in a hydrogen atmosphere at 45 p.s.i. (219.7 kg/m$^2$) in a Parr apparatus for 4 hours. After the catalyst was filtered off and the solvent evaporated, 2.3 g of a white solid product were obtained. Yield: quantitative. Differential thermal analysis: incipient decomposition at about 170° C. $[\alpha]^{25}_D = +19.6°$ [c=1% MeOH]

TLC = silica gel  Eluant = CHCl$_3$/MeOH/iPrOH/H$_2$O/AcOH
42/20/7/10.5/10.5
Rf = 0.15

Elementary analysis for C$_8$H$_{18}$ClNO$_9$S

|  | C % | H % | N % | Cl % |
|---|---|---|---|---|
| Calculated | 28.28 | 5.34 | 4.12 | 10.43 |
| Found | 28.78 | 5.34 | 4.15 | 10.23 |

$^1$H NMR (D$_2$O): δ5.68–5.59 (m, 1H, —CHOMs,); 4.05–3.75 (m, 2H, —CH$_2$N$^+$Me$_3$); 3.33 (s, 3H, CH$_3$SO$_3$—) 3.27 (s, 9H —N$^+$Me$_3$); 3.15–3.00 (m, 2H, —CH$_2$COOH)

$^{13}$C NMR (D$_2$O): δ175.192; 74.423; 70.838; 56.971; 41.662; 40.774

IR (KBr)=ν(cm$^{-1}$) 1731 (C=O), 1340 and 1174 (CH$_3$SO$_3$-)

HPLC
Column=Nucleosil 5-SA; diameter=4 mm; length=200 mm
Eluant=CH$_3$CN/KH$_2$PO$_4$ 50 mM (65/35) pH=3.5 with H$_3$PO$_4$
Flow rate=0.75 ml/min
Retention time=11.33 min
Detector=RI Waters 410

Preparation of methanesulfonyl D-(+)-carnitine chloride (5b).

10% Pd/C (500 mg) was added to a solution of methanesulfonyl D-(+)-carnitine benzyl ester chloride (5.1 g; 13.9 mmoles) in H$_2$O (60 mL) acidified to pH 4 with 1N HCl. The resulting mixture was kept under stirring in a hydrogen atmosphere, at 45 p.s.i. (219.7 kg/m$^2$) in a Parr apparatus for 4 hours.

The catalyst was filtered off and the aqueous solution lyophilized, giving 3.8 g of a white solid product. Yield: quantitative. Differential thermal analysis: it decomposes at about 150° C. $[\alpha]^{25}_D = +29.5°$ [c=1% H$_2$O]

TLC = silica gel  Eluant = CHCl$_3$/MeOH/iPrOH/H$_2$O/AcOH
42/20/7/10.5/10.5
Rf = 0.15

Elementary analysis for C$_8$H$_{18}$ClNO$_5$S

|  | C % | H % | N % | Cl % |
|---|---|---|---|---|
| Calculated | 34.84 | 6.58 | 5.10 | 12.86 |
| Found | 35.37 | 6.82 | 5.24 | 12.45 |

$^1$H NMR (D$_2$O): δ5.70–5.60 (m, 1H, —CHOMs, ); 4.06–3.75 (m, 1H, —CH$_2$N$^+$Me$_3$); 3.33 (s, 3H, CH$_3$SO$_3$$^-$) 3.27 (s, 9H —N$^+$Me$_3$); 3.15–3.00 (m, 2H, —CH$_2$COOH)

$^{13}$C NMR (D$_2$O): δ175.326; 74,530; 70,851; 56,964; 41,668; 40,914

IR (KBr)=ν(cm$^{-1}$) 1720 (C=O), 1335 and 1175 (CH$_3$SO$_3$—)

HPLC
Column=Nucleosil 5-SA; diameter=4 mm; length=200 mm
Eluant=CH$_3$CN/KH$_2$PO$_4$ 50 mM (65/35) pH=3.5 with H$_3$PO$_4$
Flow rate=0.75 ml/min
Retention time=11.38 min
Detector=RI Waters 410

Preparation of the lactone of L-(—)-carnitine chloride (6b).

NaHCO$_3$ (0.46 g; 5.4 mmoles) was added to a solution of methanesulfonyl D-(+)-carnitine chloride (1.5 g; 5.4 mmoles) in H$_2$O (25 mL) and the resulting solution was kept under stirring for 20 hours. The solution was then lyophilized, the residue taken up with CH$_3$CN and the undissolved solid filtered off. Following solvent evaporation, 0.98 g, of the title compound were obtained. Yield: quantitative.

TLC = silica gel  Eluant = CHCl$_3$/MeOH/iPrOH/H$_2$O/AcOH
42/28/7/10.5/10.5
Rf = 0.1

$^1$H NMR (D$_2$O): δ5.33–5.24 (m, 1H, —CHOCO—); 3.96–3.88 (m, 3H, —CH$_2$N$^+$Me$_3$, —CHHCOO—); 3.53–3.44 (m, 1H, —CHHCOO—); 3.24 (s, 9H, —N$^+$-Me$_3$)

$^{13}$C NMR (D$_2$O): δ172.428; 70.671; 68.094; 56.991; 41.394

IR (KBr)=ν(cm$^{-1}$) 1850 (C=O)

HPLC
Column=Nucleosil 5-SA; diameter=4 mm; length=200 mm
Eluant=CH$_3$CN/KH$_2$PO$_4$ 50 mM (65/35) pH=3.5 with H$_3$PO$_4$
Flow rate=0.75 ml/min
Retention time=19.23 min Detector=RI Waters 410

Preparation of the lactone Of L-(−)-carnitine methanesulfonate (6c).

An aqueous solution of methanesulfonyl D-(+)-carnitine chloride (1.5 g; 5.4 mmoles) was perchlorated through an IRA-402 resin (30 g) activated to $HCO_3^-$ form and cooled to 5° C., eluting with water at 5° C. till complete elution (controlled by TCL). The eluate was kept at room temperature for 4 hours. Following evaporation of the aqueous solution, 1.3 g of a raw product which was taken up with $CH_3CN$, were obtained. Evaporation of the organic solvent yielded 1 g of a white solid. Yield: 80% Differential thermal analysis: incipient decomposition at 160° C. $[\alpha]^{25}_D = +24.7°$ (c=1% MeOH)

TLC = silica gel   Eluant = $CHCl_3/MeOH/iPrOH/H_2O/AcOH$
42/28/7/10.5/10.5
Rf = 0.1

| Elementary analysis for $C_8H_{17}NO_5S$ | | | |
|---|---|---|---|
| | C % | H % | N % |
| Calculated | 40.16 | 7.16 | 5.85 |
| Found | 39.61 | 7.13 | 5.77 |

$^1H$ NMR ($D_2O$): δ5.35–5.25 (m, 1H, —CHOCO—); 3.98–3.89 (m, 3H, —$CH_2N^+Me_3$, —CHHCOO—), 3.54–3.46 (m, 1H, —CHHCOO—); 3.26 (s, 9H, —$N^+$-$Me_3$); 2.8 1 (s, 3H, $CH_3\overline{SO}_3$—)

$^{13}C$ NMR ($D_2O$): δ172.428; 70.671; 68.094; 56.991; 45.320; 41.394

IR (KBr)=ν(cm$^{-1}$) 1835 (C=O)

HPLC
Column=Nucleosil 5-SA; diameter=4 mm; length=200 mm
Eluant=$CH_3CN/KH_2PO_4$ 50 mM (65/35) pH=3.5 with $H_3PO_4$
Flow rate=0.75 ml/min
Retention time=19.48 min
Detector=RI Waters 410

Preparation of L-carnitine inner salt (7) from the lactone of L-(−)-carnitine methanesulfonate (6c).

$NaHCO_3$ (0.34 g; 4 mmoles) was added to a solution of the lactone of L-(−)-carnitine methanesulfonate (0.96 g; 4 mmoles) in $H_2O$ (20 mL) and the resulting solution was kept under stirring at room temperature for 20 hours. The solution was then percolated through AMBERLITE IR-120 resin (20 g) eluting first with water till neutrality to remove methanesulfonic acid and then with 2% $NH_3$ aqueous solution collecting the eluate till complete elution of L-(−)-carnitine inner salt (controlled by TLC).

Following evaporation of the aqueous solution, 0.64 g of L-(−)-carnitine inner salt were obtained.

Alternatively, the reaction mixture was percolated through IRA-402 resin (20 g) activated to OH$^-$ form, eluting with $H_2O$ till neutrality. The eluate was then percolated through IRC-50 resin (20 g) till complete elution of L-carnitine inner salt (controlled by TLC). Following evaporation of the aqueous solution, 0.64 g of L-(−)-carnitine inner salt were obtained. Yield: quantitative The enantiomeric excess (e.e.) was assessed via the following HPLC method, after L-(−)-carnitine was derivatized with a chiral reagent. As chiral reagent, (+)-1-(9-fluorenyl) ethyl chloroformate (FLEC) was used.

column: Nova-pak $C_{18}$(4 μ) Cartridge
length: 100 mm
diameter: 5.0 mm

| Eluant: | | |
|---|---|---|
| Solution A: | 5 mM tetrabutylammonium hydroxide (TBA$^+$ OH$^-$), | |
| | 50 mM $KH_2PO_4$ | 75 mL |
| | Acetonitrile | 25 mL |
| | brought to pH 7 with 1 N KOH | |
| Solution B: | Acetonitrile | 75 mL |
| | 5 mM $KH_2PO_4$ | 25 mL |

| Elution schedule | | |
|---|---|---|
| Time | % A | % B |
| 0 | 100 | 0 |
| 15 | 100 | 0 |
| 16 | 0 | 100 |
| 22 | 0 | 100 |
| 23 | 100 | 0 |
| 30 | stop | |

| Detector = Perkin-Elmer Fluorimeter | Excitation = 260 nm |
|---|---|
| | Slit = 10 nm |
| | Emission = 315 nm |
| | Slit = 5 nm |

L-(−)-carnitine had previously been derivatized with FLEC via the following method:

50 μL of L-(−)-carnitine solution (prepared by dissolving 10 mg carnitine in 50 mL of 50 mM TBA$^+$OH$^-$ brought to pH 7 with concentrated $H_3PO_4$) and 200 μL of solution consisting of 1 mL FLEC in 3 mL acetone, were kept under stirring at 80° C. for 20 minutes.

The solution was cooled and 4 mL of solution A were added thereto, 5 μL of the resulting solution were injected L-(−)-carnitine $K^1=5.79$ D-(+)-carnitine $K^1=4.82$, absent $$e \cdot e = \frac{L - D}{L + D} \times 100 = 100\%$$

Preparation of L-carnitine inner salt (7) from methanesulfonyl-D-carnitine chloride (5b).

$NaHCO_3$ (0.46g; 5.4 mmoles) was added to a solution of methanesulfonyl-D-carnitine chloride (1.5 g; 5.4 mmoles) in $H_2O$ (25 mL) and the resulting solution was kept under stirring at room temperature for 20 hours. Further $NaHCO_3$ (0.46; 5.4 mmoles) was then added and the solution was kept under stirring at room temperature for further 20 hours. The title compound was isolated as previously described for the isolation of 7 from 6 b.

L-carnitine is obtained from methanesulfonyl-D-carnitine through the formation of the lactone 6, as evidenced by NMR, HPLC, IR and TLC analysis carried out on a sample obtained by lyophilizing a portion of the solution 20 hours following first $NaHCO_3$ addition.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A lactone of L-(−)-carnitine of the formula 6

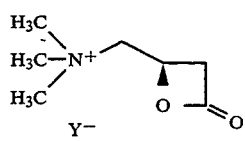

wherein Y⁻ is any monovalent counterion.

2. The lactone of claim 1, wherein Y⁻ is a halogen, acid sulphate, acid phosphate, perchlorate, metaperiodate, tetraphenylborate or alkylsulphonate.

3. The lactone of claim 1, wherein Y⁻ is chloride.

4. The lactone of claim 1, wherein Y⁻ is methanesulfonate.

5. The lactone of claim 1, wherein Y⁻ is perchlorate.

6. The lactone of claim 1, wherein Y⁻ is an alkyl sulfonate having 1–12 carbon atoms.

7. The lactone of claim 1, wherein Y⁻ is dodecylsulfonate.

* * * * *